(12) United States Patent
Egli et al.

(10) Patent No.: US 9,420,984 B2
(45) Date of Patent: Aug. 23, 2016

(54) METHOD AND DEVICE FOR ASSISTING IN THE TREATMENT OF BONE FRACTURES

(71) Applicant: SIEMENS AKTIENGESELLSCHAFT, Munich (DE)

(72) Inventors: Adrian Egli, Sursee (CH); Rainer Graumann, Hoechstadt (DE); Adrian John, Kaisten (CH); Gerhard Kleinszig, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 295 days.

(21) Appl. No.: 14/270,765

(22) Filed: May 6, 2014

(65) Prior Publication Data

US 2014/0328460 A1    Nov. 6, 2014

(30) Foreign Application Priority Data

May 6, 2013 (DE) ......................... 10 2013 208 285

(51) Int. Cl.
| | |
|---|---|
| *A61B 6/00* | (2006.01) |
| *A61B 6/03* | (2006.01) |
| *A61B 6/12* | (2006.01) |
| *G06T 7/00* | (2006.01) |
| *A61B 19/00* | (2006.01) |
| *A61F 2/30* | (2006.01) |
| *G05B 19/4099* | (2006.01) |
| *G06F 19/00* | (2011.01) |
| *A61B 17/80* | (2006.01) |

(52) U.S. Cl.
CPC .............. *A61B 6/505* (2013.01); *A61B 6/032* (2013.01); *A61B 6/12* (2013.01); *A61B 6/5211* (2013.01); *A61B 6/5235* (2013.01); *G06T 7/0028* (2013.01); *A61B 17/80* (2013.01); *A61B 19/50* (2013.01); *A61B 34/10* (2016.02); *A61F 2/30942* (2013.01); *G05B 19/4099* (2013.01); *G06F 19/321* (2013.01); *G06F 19/3437* (2013.01); *G06T 2207/10116* (2013.01); *G06T 2207/30052* (2013.01)

(58) Field of Classification Search
CPC .............................. A61B 19/50; A61B 34/10
See application file for complete search history.

(56) References Cited

U.S. PATENT DOCUMENTS

| | | | |
|---|---|---|---|
| 8,886,496 B2 * | 11/2014 | Graumann | ............. A61B 19/50 703/1 |
| 2008/0074427 A1 | 3/2008 | Barth | |

(Continued)

FOREIGN PATENT DOCUMENTS

| | | |
|---|---|---|
| DE | 102006048451 A1 | 4/2008 |
| DE | 102007034221 A1 | 4/2008 |
| WO | 2012113030 A1 | 8/2012 |

*Primary Examiner* — Andrew Yang
(74) *Attorney, Agent, or Firm* — Laurence Greenberg; Werner Stemer; Ralph Locher

(57) ABSTRACT

A bone fracture is treated by employing a database with comparison data records. The records each include at least one 3D image data record of at least one bone. Each comparison data record is assigned to an examination object, into which a comparison implant was implanted prior to recording the 3D image data record. A two-dimensional x-ray image of a target bone is generated. A 2D/3D registration of the x-ray image with 3D image data records is effected and a deviation value is calculated for each comparison data record. A reference data record is determined by selecting the comparison data record that includes the 3D image data record with the lowest deviation value. An implantation parameter is determined which describes a parameter of the implant and/or of a fastening element for fastening the implant, using the reference data record and/or displaying data of the reference data record on a display.

18 Claims, 6 Drawing Sheets

(56) References Cited

U.S. PATENT DOCUMENTS

| | | |
|---|---|---|
| 2011/0093108 A1 | 4/2011 | Ashby et al. |
| 2012/0010710 A1* | 1/2012 | Frigg ............... A61B 19/50 623/16.11 |
| 2012/0274631 A1* | 11/2012 | Friedland ............... A61B 19/50 345/419 |
| 2013/0332128 A1 | 12/2013 | Miles et al. |

\* cited by examiner

METHOD AND DEVICE FOR ASSISTING IN THE TREATMENT OF BONE FRACTURES

CROSS-REFERENCE TO RELATED APPLICATION

This application claims the priority, under 35 U.S.C. §119, of German patent application DE 10 2013 208 285.1, filed May 6, 2013; the prior application is herewith incorporated by reference in its entirety.

BACKGROUND OF THE INVENTION

Field of the Invention

The invention relates to a method and a device for assisting a user in the treatment of bone fractures using a stabilization implant.

Bone fractures are often treated by attaching an implant to a bone. An advantage of employing implants in the treatment of bone fractures is that stresses again can be exerted onto the bone within a short period of time. Moreover, the bone fragments are fixed at the right position, as a result of which a reliable recovery of the bone can be achieved, particularly in the case of complex fractures. The implants often consist of plates that are fastened to the fractured bone. During the implantation, a decision has to be made by the treating medical practitioner in respect of the position at which the implant is to be arranged and how fastening screws, by means of which individual bone fragments are fixed, are applied. The angle at which fastening elements are applied to the bone for the purposes of fastening the implant can be selected in a multiplicity of implants. At the same time, it is necessary to prevent a fastening element from penetrating through the bone and entering the tissue or a joint.

The standard process for setting the position of the implant and the position of the fastening elements lies in recording a plurality of x-ray images during surgery and using these to plan and verify the implantation. However, the operator in this case not only has to estimate a possible ideal arrangement of the implant from a few individual two-dimensional x-ray images, but also what fastening elements are employed for fastening the implant, in particular how long the employed fastening elements are, and at what angle they are introduced into the implant. Modern implants often permit a variation of a screw angle within an angular range of approximately +/−15°. Although this improves the option of fastening bone fragments to the implant, it also increases the risk of penetrating through the bone and damaging the surrounding tissue or a joint. Moreover, in conditions during surgery, it may be difficult to record x-ray images from various perspectives, and so often only a single projection of the bone is available for planning and verifying the implantation.

SUMMARY OF THE INVENTION

It is accordingly an object of the invention to provide a method and a device for aiding in the setting of bone fractures which overcome the above-mentioned disadvantages of the heretofore-known devices and methods of this general type and which provides for an improved method for assisting a user in the treatment of bone fractures using a stabilization implant.

With the foregoing and other objects in view there is provided, in accordance with the invention, a method for assisting a user in a treatment of bone fractures using a stabilization implant, the method comprising:

accessing a database having stored therein a multiplicity of comparison data records, the comparison data records each containing at least one 3D image data record of at least one bone, wherein each comparison data record is assigned to an examination object, into which a comparison implant was implanted prior to recording the 3D image data record;

with an x-ray instrument, recording at least one two-dimensional x-ray image of a target bone to which the stabilization implant is to be fastened;

with a computer apparatus, 2D/3D registering the x-ray image with 3D image data records of a selection of the comparison data records determined by a selection criterion or of all comparison data records and calculating a deviation value, the deviation value being a measure for a deviation of the 3D image data record registered with the x-ray image from the x-ray image, for each comparison data record for the 3D image data record of which a 2D/3D registration was performed by a computer apparatus;

with the computer apparatus, determining a reference data record by selecting the comparison data record with the lowest deviation value; and with the computer apparatus, determining at least one implantation parameter describing a parameter of the implant and/or of a fastening element for fastening the implant, using the reference data record and/or displaying data of the reference data record on a display device of the computer apparatus.

In other words, the objects are achieved by virtue of the fact that a database is employed, in which a multiplicity of comparison data records are stored, which comparison data records each comprise at least one 3D image data record of at least one bone, wherein each comparison data record is assigned to an examination object, into which a comparison implant was implanted prior to recording the 3D image data record, comprising the following steps: by means of an x-ray instrument, recording at least one two-dimensional x-ray image of a target bone, to which the stabilization implant is intended to be fastened, by means of a computer apparatus, 2D/3D registering of the x-ray image with 3D image data records of a selection of the comparison data records determined by a selection criterion or of all comparison data records and calculating a deviation value, which is a measure for the deviation of the 3D image data record registered with the x-ray image from the x-ray image, for each comparison data record for the 3D image data record of which a 2D/3D registration was performed, by means of the computer apparatus, determining a reference data record by selecting the comparison data record with the lowest deviation value, by means of the computer apparatus, determining at least one implantation parameter, which describes a parameter of the implant and/or of a fastening element for fastening the implant, using the reference data record and/or displaying data of the reference data record on a display device.

The concept underlying the invention is that stabilization implants for treating bone fractures are often arranged in a relatively similar manner since human bones often do not have great variation in typical fracture regions within specific patient groups and since the regions in which fractures occur are also similar. Therefore, the assumption can usually be made that data relating to an implantation, which corresponds to an implantation to be performed or which at least was performed in a similar bone, are already stored in a database comprising data about a multiplicity of preceding implantation procedures.

If such a database of preceding implantations is available, it is necessary to select a fitting data record for the current implantation and it is necessary to check which implantation parameters can be taken over from this data record. In order to establish a fitting comparison data record from a preceding examination, a two-dimensional x-ray image of the target bone, on which the stabilization implant is to be fastened, is initially recorded within the scope of the method according to the invention. This x-ray image can be recorded using any x-ray instrument, for example using a C-arm. Naturally, it is also possible within this step to record a plurality of images in order to improve selection and registration of the comparison data record. However, within the scope of the method according to the invention, this is not mandatory.

In the next step of the method according to the invention, it is intended to establish which earlier implantation corresponds best to the implantation to be carried out. This is to be equated to the selection of a comparison data record. The comparison data records employed for this were already stored in a database in advance. It is essential that a stabilization implant was implanted prior to recording the 3D image data record for each examination object for which a comparison data record is present. At least one 3D image data record should be available for each comparison data record. By way of example, the 3D image data record can be a CT recording of the examination object. However, the 3D image data record can also be already segmented image data or image data from other imaging modalities.

In order to ensure high quality of the comparison data records, only data records of examination objects, in which the implantation performed was considered to be successful, are to be stored as comparison data records. The 3D image data records could be verification data records, i.e. recordings of examination objects for three-dimensional verification of the correct fit of the stabilization implant. In this case, the target bone and the stabilization implant and the fastening elements are imaged in the 3D image data record. However, it is often advantageous to employ as comparison data records data records which were recorded after the stabilization implant has been removed again.

In addition to the 3D image data records, the comparison data records can contain a multiplicity of further items of information. Thus, for example, additional segmentation information, which specifies the type and/or other specifications, e.g. dimensional specifications, of the implant or of the fastening elements, the position and/or orientation of the implant and/or of the fastening elements or other specifications in respect of the performed implantation, the age of the patient, the sex of the patient or the like, can be stored in the comparison data record.

In particular, this additional information can be employed to make a pre-selection of the comparison data records, with the 3D image data record of which a 2D/3D registration with the x-ray image is intended to be performed. 2D/3D registrations may require high computational costs. Since a database comprising a multiplicity of implantation procedures of the stabilization implants may, under certain circumstances, be very large, it is advantageous to reduce the number of 3D image data records with which a 2D/3D registration with the x-ray image is carried out. Thus, for example, it is possible to employ only those data records in which the same bone was fractured and/or in which the age of the further examination object lay close to the age of the patient whose bone fracture is intended to be treated.

2D/3D registrations are an active field of research. Therefore, 2D/3D registration is only to be explained here on the basis of a few exemplary embodiments. Thus, for example, it is possible initially to generate a projection image in a specific projection direction from the 3D image data record which is intended to be registered to the 2D x-ray image. The projection direction can be established from a known recording direction of the 2D x-ray image and from a known orientation of the 3D image data record. However, it is also possible to establish it within the scope of the registration method. As soon as such a projection image is produced, the 2D/3D registration can be performed like a normal 2D/2D registration.

By way of example, in this case it is possible to employ directly a correlation function between these two images. Alternatively, it is also possible initially to use an edge detector and the images can subsequently be correlated. A detection of features, for example by a scale-varying feature transformation, in one of the images and a subsequent detection of these features in the second image is also possible. Compared to a direct correlation of the images, approaches based upon feature, corner or edge detection are advantageous in that it is possible, under certain circumstances, to detect distortions between the images and possibly to deduce a correction of the projection direction from these.

Alternatively, or in addition thereto, it is also possible to perform the 2D/3D registration using segmentation algorithms or already available segmentation data. In this case, it is only still necessary to bring into correspondence the segmented regions or the boundaries thereof. To this end, methods are known for both two-dimensional and three-dimensional registration.

A deviation value is established for each 3D image data record, and hence for each comparison data record comprising this data record, after the registration or even during the registration. A multiplicity of registration methods already employ a minimization of a deviation value in order to optimize a registration. In these cases, it is possible to employ this value as deviation value for the ideal registration. However, it is also possible initially to carry out an image registration and subsequently to carry out e.g. a 2D projection of the 3D image data record and calculate a cost function, for example a standard deviation, between the two 2D images. It is often advantageous to apply this cost function to processed image data, i.e. those which were already treated by an edge detector or the like.

After a deviation value is determined for each comparison data record, the comparison data record with the lowest deviation value is determined to be the reference data value. It should be noted here that although this step is described as taking place after the step of 2D/3D registration and determining the deviation value, a mixture between these steps naturally also is possible. In particular, in the case of systems with little memory, it may be advantageous to keep only few deviation values and data records in the memory. By way of example, in this case a check can be carried out after each registration as to whether a deviation value is less than a previously calculated deviation value and, if this is the case, storing the data record as potential reference data record. The stored potential reference data record after working through all 3D image data records then is the actual reference data record. A multiplicity of further implementations are likewise conceivable; however, these all lead to the same result, namely determining the comparison data record which comprises the 3D image data record with the lowest deviation value as reference data record.

In the simplest case, it is possible to employ the reference data record so as to provide the user a display of the 3D image data record of the reference data record. This shows to the user a bone with or without an implant fastened thereto, which is very similar to the bone into which the implant should be introduced. Naturally, it is also possible in this case to display and position virtual implant models or models of fastening elements together with the 3D image data record. This renders possible planning the implant in three dimensions, as a result of which the planning quality and safety can markedly be improved.

Alternatively, or in addition thereto, it is however also possible to determine directly one or more implantation parameters. Thus, for example, it is possible to propose directly a position of the implant, an implant type, the length or type of a fastening element or else the introduction angle of a fastening element. In particular, a very powerful planning system, which can be used very easily, is developed by the representation of the 3D image data record already described above since this renders it possible to propose to the user a multiplicity of implantation-relevant parameters and immediately display these visually on a 3D model based upon the data of the comparison data record, and renders it possible for the user to adapt said parameters in an interactive manner.

It is possible that, by means of the computer apparatus, a comparison implant imaged in the 3D image data record is segmented prior to storing the comparison data record comprising the 3D image data record in the database or when recalling this comparison data record from the database, wherein, in particular, the segmented comparison implant is not considered during the registration and calculation of the deviation value. This is particularly advantageous if verification recordings, i.e. recordings which were made to check the correct seat of an implant, are stored in the database; however, the method according to the invention is to be employed in a phase of the implantation planning in which the implant is not yet arranged on the target bone. In this case, the 3D image data records also comprise the implant. Such implants, which are often made from metal, exhibit a very strong contrast, in particular if CT data records are employed. These 3D image data records are now intended to be registered with a 2D x-ray recording in which no implant is imaged. This can lead to significant errors in the registration. It is therefore advantageous to establish the position and extent of the implant and not to employ the points in the 3D image data record covered by the implant for registration with the x-ray image and for determining the deviation value.

However, segmenting the implant is also advantageous in that it is possible to obtain implantation parameters directly. Thus, for example, angles of fastening elements can easily be detected in the segmentation and provided immediately as implantation parameter after selecting a comparison data record as reference data record. The same applies to the position and length of the fastening elements, and to the position and orientation of the implant itself.

The implantation parameters can be determined in various ways. Thus, it is possible that the implantation parameter or at least one of the implantation parameters is determined by a user by taking over a comparison parameter stored in the reference data record, which comparison parameter describes a parameter of the comparison implant or of a comparison fastening element, and/or calculating from the 3D image data record of the reference data record, wherein, in particular, a segmentation of the 3D image data record is employed and/or a bone model is adapted to the 3D image data record, and/or outputting at least one superposition of a two-dimensional representation of the 3D image data of the reference data record and a two-dimensional representation of a three-dimensional implant model and/or of at least one three-dimensional fastening element model on the display device and interactively adapting the implant model and/or the fastening element model.

In the simplest case, comparison parameters are already stored in the reference data record. Thus, it is possible that implantation parameters, such as e.g. the implant type, the implant position, the type of the used fastening elements or the like, which were used in the preceding implantation, are stored. This is possible if these parameters were entered manually. Thus, for example, it is possible that software employed for planning the implantation adds these parameters to a patient data record and this patient data record is anonymized during the creation of the comparison data record and included in the comparison data record. However, additionally or alternatively, it is also possible for the implantation parameters to have been obtained from a preceding segmentation of the 3D image data, for example when verifying the implantation.

Naturally, implantation parameters can also be obtained directly from the 3D image data record of the reference data record. By way of example, if an implant is imaged in this data record, it is possible, as already described above, for the implant to be segmented in the data record and for the parameters or at least some of the parameters of the implant and of the fastening elements to be obtained from this segmentation. Moreover, it is possible to obtain a bone model from the 3D image data record. The bone model can be calculated by segmenting the data record or by adapting an available bone model to the 3D image data record. The bone model established thus then can be employed to optimize the implantation parameters. Thus, it is possible to adapt angles and lengths of fastening elements in order to achieve an ideal hold, without penetrating through the bone and putting the tissue or joints at risk. With the aid of these parameters, it is also possible to determine particularly advantageous positions of the implant or the implant type. If the complete bone model is known, the adaptation of the implant can simply be considered to be a multidimensional optimization problem and, as such, be solved, wherein the parameters in respect of which the optimization takes place could be e.g. a maximum length of the fastening elements and a cover of the fracture region by the implant which is as large scale as possible.

As mentioned at the outset, it is also possible to depict a superposition of the 3D image data of the reference data record on an implant model. If it is possible to adapt the parameters of the implant model or of the fastening element models interactively in this superposition, this can also be employed for planning the implantation, wherein the implantation parameters can be determined automatically. Naturally, the above-described processes for establishing implantation parameters can also be mixed and individual parameters may be prescribed by a user.

It can often be computationally very expensive to perform a 2D/3D registration if the direction of the 2D recording in relation to the 3D image data record is unknown. It is therefore advantageous if, within the step of 2D/3D registration, an orientation and/or location specification of the recording stored in the comparison data record is employed to restrict a search space of the registration parameters. In this case, the projection direction and the advance of the image data can be optimized in a small angular range or for small local displacements, which significantly accelerates a registration.

A further significant acceleration of the method can be achieved if the number of examined comparison data records is restricted. As mentioned previously, this is possible with the aid of a selection criteria. It is possible that the selection criterion for selecting the comparison data records is a comparison of at least one item of additional information of the imaged bone stored with the comparison data record, in particular an age of the patient, a comparison of a bone diameter and/or of information relating to the comparison implant, or a comparison of an image parameter, in particular a parameter determined by segmenting the 3D image data record, determined from the respective 3D image data record by the computer apparatus, with a predetermined or predeterminable value, in particular the upper or lower boundary of a value interval. Thus, for example, it is possible to determine a maximum and minimum bone diameter for the comparison data records from the diameter of a bone in the x-ray image. A search can then be performed quickly if such a parameter is already stored in the comparison data records. However, this is not always the case, and so such a parameter can also be determined directly from the 3D image data records.

It is possible that the implantation parameter is displayed on the display device, wherein the representation is, in particular, graphical by displaying an implant model and/or at least one fastening element model. Using such a display, the parameters can be detected particularly easily by a user. Moreover, such a display can be employed for interactive adaptation of the parameters, as mentioned previously.

Transfer of information obtained from a smaller bone to a larger bone, or vice versa, is often not possible. It is therefore advantageous in the method according to the invention if size information is available for the x-ray image and the 3D image data records. Such size information is automatically available if a known implant is imaged in the x-ray image or in the 3D image data records. However, if the method according to the invention is to be employed for planning an implantation, an implant is generally not situated in the image region. It is therefore advantageous if, prior to recording the x-ray image, a calibration body is arranged in the image region of the x-ray image for size calibration. This calibration body should advantageously be arranged level with the target bone. Naturally, it is also possible to employ other methods for establishing a magnitude scale. Under certain circumstances, it may also be advantageous to employ a calibration body for recording the 3D image data records. However, for example, it is also possible to obtain a magnitude scale by a stabilization implant present in the image region or to employ known calibrations of the recording apparatus.

A multiplicity of bones are present in a mirror-symmetric manner in the human body. In order to achieve a higher efficiency of the employed database, it is therefore possible that, for target bones which are present twice in the body of the examination object and present in a mirror-symmetric manner, comparison data records, the 3D image data record of which images not the target bone but the bone mirror-symmetrical to the target bone, are also used when registering and calculating the deviation value, wherein the x-ray image or the 3D image data record is mirrored in this case.

Registering the x-ray image with the 3D image data record and hence establishing the correct reference data record or the correct comparison parameters is particularly simple if the stabilization implant is imaged both in the 3D image data record and in the x-ray image. Moreover, it can be advantageous to determine further implantation parameters in the case of an implant already arranged on the bone. Therefore, it is possible that, after introducing the implant into the body of the examination object, at least one further x-ray image is recorded and at least one implantation parameter is determined anew and/or a further implantation parameter is determined.

Using the method according to the invention, it is possible to determine all or a selection of the implantation-relevant parameters. Thus, the implantation parameter or one of the implantation parameters can be an implant type, an implant position, a fastening element type, a fastening element length and/or an introduction angle of at least one fastening element. In particular, the fastening elements can be screws. In this case, it is also possible to establish parameters which describe the screw head, the thread or the like.

There often is only limited computational capacity available at the location of an operation and quick results are to be depicted to the user of the method. It is therefore advantageous if a 3D image data record is segmented prior to storing the comparison data record comprising the 3D image data record in the database and the segmentation data are stored in the comparison data record, wherein the segmentation data are employed in the 2D/3D registration and/or the calculation of the deviation value and/or of the implantation parameter. In particular, it is also possible for such segmentation to be checked and/or corrected prior to storing the comparison data record.

Moreover, it is possible that, prior to storing the comparison data record in the database or when recalling the comparison data record from the database, the comparison implant in the 3D image data record is segmented and registered with a model implant by the computer apparatus and the coordinate system of the 3D image data record is transformed into a coordinate system of the model implant. This is advantageous in particular if a stabilization implant is imaged both in the 3D image data record and in the x-ray image in such a way that it is already situated at a final position. In this case, a 2D/3D registration is no longer necessary since the 3D image data record is already registered onto the implant. Naturally, a 2D/3D registration can subsequently still be carried out with restricted parameter space in order to improve further the registration result.

With the above and other objects in view there is also provided, in accordance with the invention, a device for assisting a user in the treatment of bone fractures using a stabilization implant. The device includes:

a storage apparatus for providing a database in which a multiplicity of comparison data records are stored, which comparison data records each comprise at least one 3D image data record of at least one bone, wherein each comparison data record is assigned to an examination object, into which a comparison implant was implanted prior to recording the 3D image data record, a registration apparatus for 2D/3D registration of a previously recorded x-ray image with 3D image data records of a selection of the comparison data records determined by a selection criterion or of all comparison data records, a calculation apparatus for calculating a deviation value, which is a measure for the deviation of the 3D image data record registered with the x-ray image from the x-ray image, for each comparison data record for the 3D image data record of which a 2D/3D registration was performed, a reference determination apparatus for determining a reference data record by selecting the comparison data record with the lowest deviation value, an implant parameter determination apparatus for determining at least one implantation parameter, which describes a parameter of the implant and/or of a fastening element for fastening the implant, using the reference data record and a display device for outputting the representation of the data of the reference data record or of the established implantation parameters.

The device is embodied, in particular, for carrying out at least one method described in the preceding text. All embodiments in respect of the method according to the invention can be transferred analogously to the device according to the invention, by way of which the aforementioned advantages likewise are obtained.

As is known in principle, the components of the device can be realized by one or more computer apparatuses and corresponding hardware and/or software constituents.

Other features which are considered as characteristic for the invention are set forth in the appended claims.

Although the invention is illustrated and described herein as embodied in a method and device for assisting in the treatment of bone fractures, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
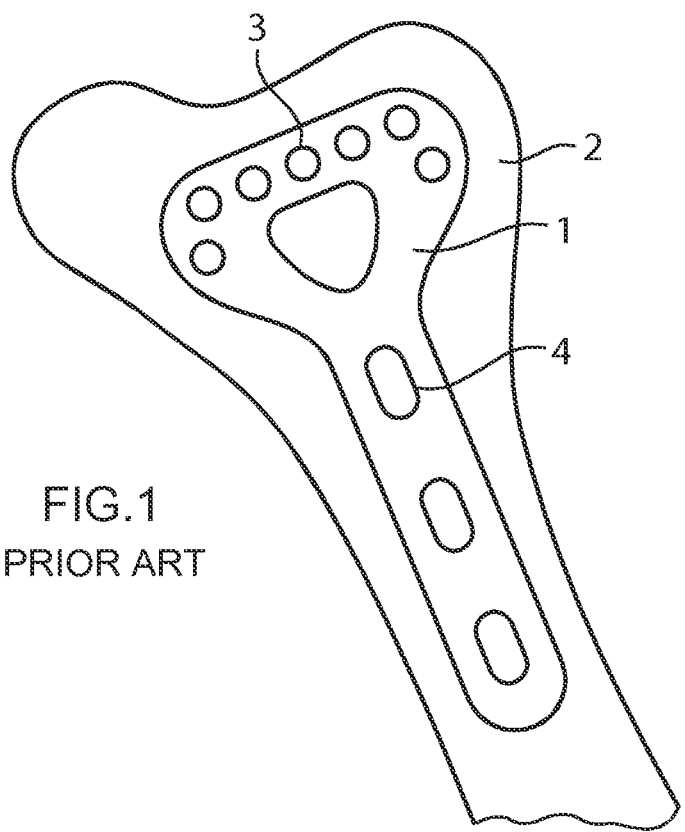
FIG. 1 shows, in an exemplary manner, the arrangement of an implant on a radius bone.

Referring now to the figures of the drawing in detail and first, particularly, to FIG. 1 thereof, there is shown an assembly, known from the prior art, of a stabilization implant 1 on a bone 2. The stabilization implant 1 substantially has the form of a plate with a plurality of holes. It may be angled to have a better fit to the bone. The angling is usually predetermined and is not modified within the scope of fitting to the patient. The stabilization implant 1 has a multiplicity of openings 3 and 4 for introducing fastening elements. Some of the openings 3 set the position of the fastening element, but allow a variation of the angle of the fastening element in a range of, say, 30°. However, after the fastening element has been introduced, this angle is set and can no longer be changed. Other openings 4 for introducing fastening elements allow a shift of the fastening element in one or two dimensions. The fastening elements serve firstly to fasten the stabilization implant 1 on the non-fractured part of the bone 2 and secondly to fasten bone fragments in such a way that they can grow back with the bone. When planning the arrangement and fastening the implant, it is essential that a hold of the implant, which is as good as possible, on the bone and on the bone fragments is ensured, wherein penetrating through the bone and hence damaging the tissue and/or a joint is to be avoided. During surgery, x-ray recordings for planning the arrangement and fastening of the stabilization implant 1 are often only available from one perspective. This should be improved using the method described.

Figure 2:
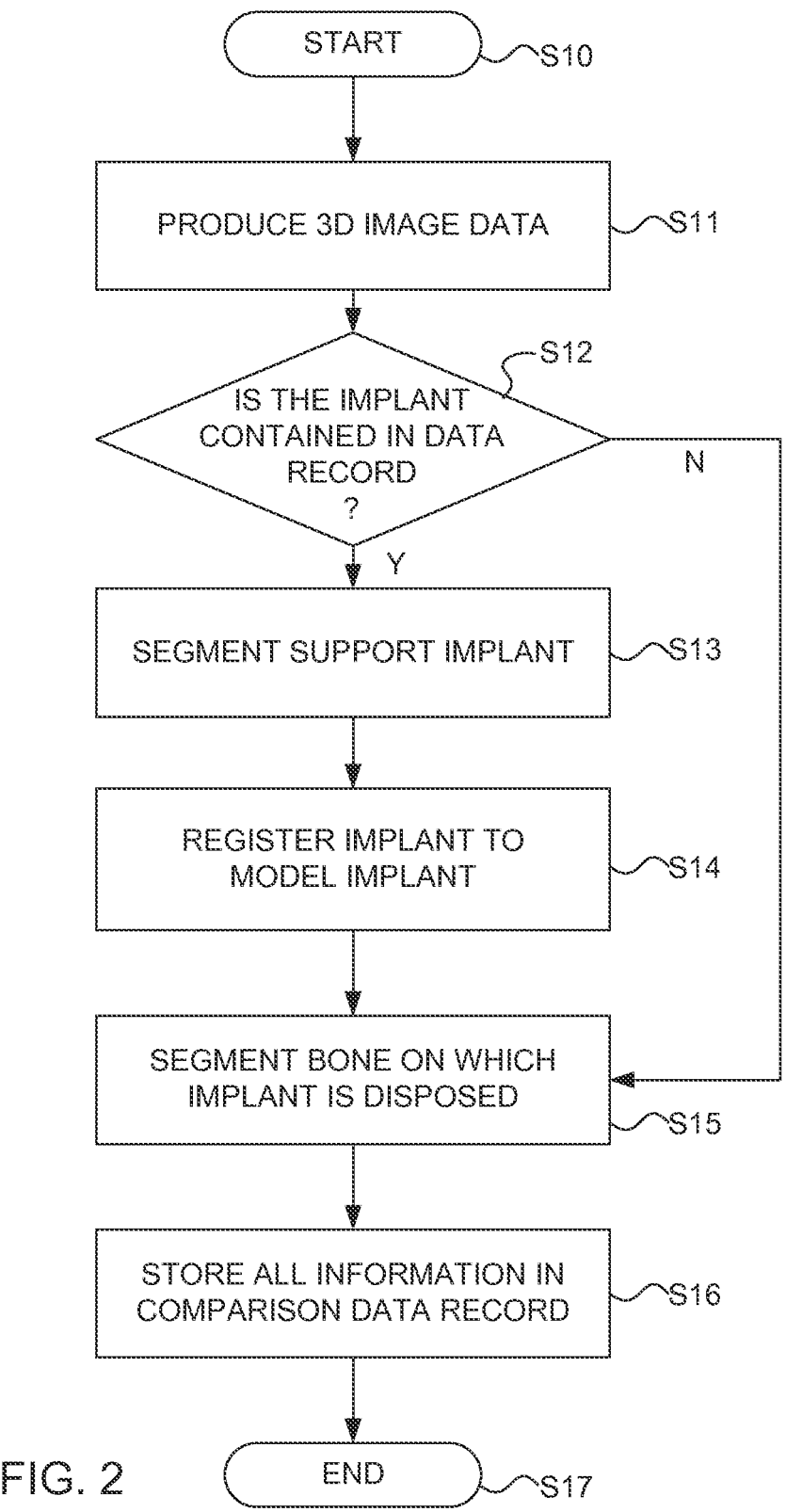
FIG. 2 is a flowchart for producing a comparison data record for the database employed in the method according to the invention.

In the described method, comparison data records of earlier implantations are employed. FIG. 2 shows a flowchart relating to how such a comparison data record can be produced. The method shown in FIG. 2 is usually only used after an implantation was considered to be a success. However, it is also possible already to employ the method in the verification phase of the implantation and subsequently to discard data records originating from implantations which were assessed to be unsuccessful or no good.

After the start of the method in step S10, a three-dimensional image data record of a bone, on which a stabilization implant was previously implanted, is produced in step S11. It is possible that the stabilization implant is still situated on the bone at the time at which the image is recorded in step S11; however, it is also possible to record an image recording of an already healed bone without implant. By way of example, the 3D image data are recorded by a computed tomography scanner.

In step S12, it is determined whether a stabilization implant is situated in the image region of the 3D image data record recorded in step S11. It is possible for a user to manually set, either already prior to the image recording in step S11 or after the image recording in step S11, whether or not a stabilization implant is situated on the bone. However, alternatively, an image detection algorithm can be employed in step S12 to determine whether the image data record recorded in step S11 comprises a stabilization implant. Such a stabilization implant can easily be detected, at least in a CT recording, since such implants are often made of metal and therefore have a high x-ray absorption coefficient.

If no stabilization implant is imaged in the 3D image data record, the method continues directly in step S15. If a stabilization implant is contained in the 3D image data record, the former is segmented in step S13. Due to the high absorption coefficient for x-ray radiation of most stabilization implants, a segmentation of the support implant is usually possible in a simple, robust and highly resolved manner. Therefore, further information about the implant, such as e.g. the implant position and orientation and at least the length, the location and the orientation of the fastening elements, can be obtained during the segmentation of the implant in step S13 too. These data can be stored in the comparison data record in a subsequent step.

The implant segmented in step S13 can moreover be registered to a model implant in step S14, particularly if the comparison data record is also intended to be employed for registration to x-ray images which likewise image a stabilization implant. This registration to a model implant can be employed firstly for determining implantation parameters; secondly, the 3D image data record can be transformed after the registration into a coordinate system corresponding to the coordinate system of the model implant. This has a number of advantages. Firstly, in the case of a known type of model implant, it is possible to determine a magnitude scale for the 3D image data record by this registration and coordinate transform and ensure that all 3D image data records which are stored in comparison data records have a common magnitude scale. This common magnitude scale significantly simplifies the use of comparison data records from different sources. Secondly, the 2D/3D registration or the determination of a deviation parameter for cases in which a stabilization implant is imaged in the x-ray image can be substantially accelerated due to this preparing transform. This will still be explained in more detail below with reference to FIG. 5.

A segmentation of at least the bone on which the stabilization implant is situated is subsequently carried out in step S15, irrespective of whether a stabilization implant is situated in the image region of the 3D image data record. Additionally, it is also possible to segment further bones or other organs in order to simplify a subsequent registration of the 3D image data record to the x-ray image. Segmenting the 3D image data already prior to storing the comparison data record is advantageous in that, in particular, the intrasurgical part of the method is less computationally expensive in this case. This renders it possible, firstly, to reduce the required computational power of the instrument in the operating theater and, secondly, to accelerate the method, as a result of which it is possible to achieve a shorter time of operation. Similar to the segmentation of the implant in step S13, it is also already possible to determine parameters of the bone, such as e.g. the diameter of a bone or the like, during the segmentation of the bone in step S15.

In step S16, all obtained data, i.e. at least the 3D image data record and further information relating to the bone and/or implant segmentation, patient information, bone parameters or implantation parameters, are stored together in the comparison data record. The comparison data record can be stored as a single document; however, it is also possible e.g. to store the comparison data record in a database. By way of example, a core data record can contain only parameters which require relatively little storage space, such as bone type, age, bone diameter or the like, and relatively comprehensive data, such as e.g. those of the 3D image data record, can be stored only as references. However, a multiplicity of different formats are also possible. In particular, the comparison data record can also be stored in a format which renders it possible to display parts of the comparison data record in conventional treatment planning systems or further systems for displaying medical data records from different data sources.

After storing the comparison data record, the method is completed in step S17. As already mentioned previously, it is possible that a comparison data record is already produced before the operation result is evaluated. In this case, the comparison data record can also be used for evaluating the operation result and the comparison data record can be discarded if the implantation result was found to be no good.

Figure 3:
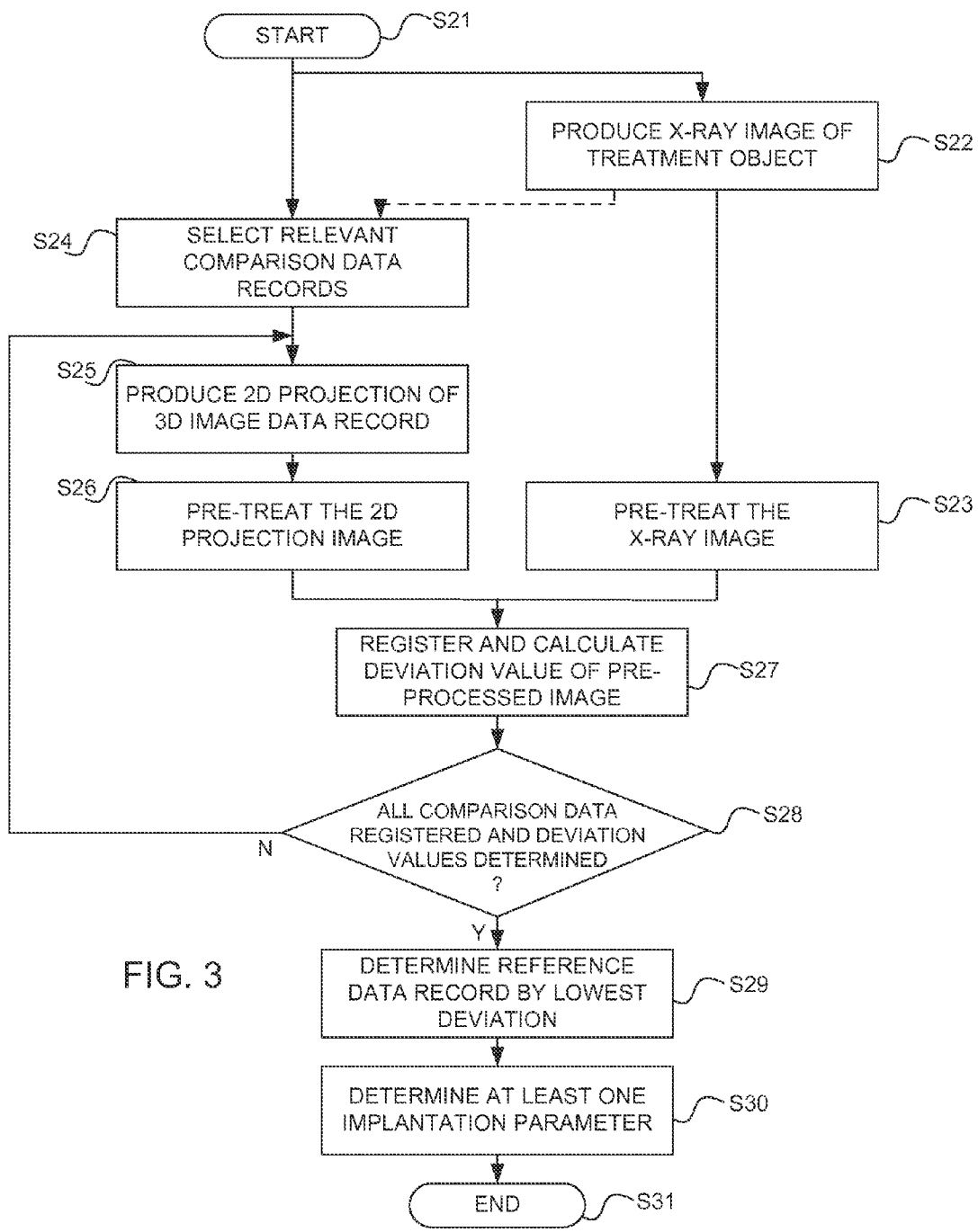
FIG. 3 is a flowchart of an exemplary embodiment of the method according to the invention.

FIG. 3 shows a first exemplary embodiment of the method for assisting in the treatment of bone fractures using a stabilization implant. At the start of the method in step S21, a database with a multiplicity of comparison data records is already available. Moreover, a treatment object, the bone fracture of which is to be treated, has been prepared in such a way that x-ray images of the treatment object can be produced and the stabilization implant can be implanted in the treatment object. Then, in step S22, an x-ray image of the treatment object is initially produced. The image region of the x-ray image is selected in such a way that the bone on which the stabilization implant is to be fixed is situated in the image region. In the exemplary embodiment described here, the assumption is made that the stabilization implant is still situated outside of the body and therefore not in the image region of the x-ray image. Thus, during the further course of the method, a bone is to be established from the comparison data records, which bone is as similar as possible to the target bone of the treatment object.

In order to simplify the determination of the reference data record, there can be a pre-treatment of the x-ray image in step S23. In this step, the x-ray image is treated in such a way that a subsequent registration in step S27 is simplified. By way of example, there may be an edge detection, in particular by applying a Sobel operator to the x-ray image or else a detection of corners or scale-invariant features.

In parallel with recording and processing the x-ray image, it is possible to select comparison data records and prepare these for registration. In step S24, the relevant comparison data records are initially selected. Thus, it is possible that comparison data records for a multiplicity of bones are stored in a database. In this case, only the comparison data records relating to a bone corresponding to the target bone are to be selected. Additionally, it is possible to apply a multiplicity of further selection criteria. Thus, the age of the examination object from which the comparison data record originates can be restricted to an age range corresponding to the age range of the treatment object. In certain circumstances, it is also already possible to employ information in step S24 which is obtained from the x-ray image recorded in step S22. By way of example, a bone diameter of the x-ray image recorded in step S22 can be detected in step S24 and it is possible to select only comparison data records relating to a bone having a similar bone diameter.

Additionally, a multiplicity of further selection criteria are feasible for restricting the selection of the relevant comparison data records already prior to the registration, and can be applied in step S24.

After determining a selection of comparison data records in step S24, a 2D projection of the 3D image data record contained in the comparison data record is produced in step S25. The production of a 2D projection enables a particularly simple registration of the 3D image data with the x-ray image since only two-dimensional data have to be registered. If the orientation of the 3D image data record is known, the projection direction can be fitted to the recording direction of the x-ray image. If the orientation is unknown, a predefined number of projection images, which correspond to different projection directions, can be produced. Then, the projection direction can be adapted within the scope of the registration method and a new projection can be calculated for the newly determined projection direction.

After calculating the 2D projection in step S25, a processing step equivalent to the processing step applied to the x-ray image in step S23 is applied to the 2D projection image in step S26. By way of example, it is also possible in this case to employ an edge detection or a scale-invariant feature detection. In step S27, the x-ray image pre-processed in step S23 and the 2D projection pre-processed in step S26 are registered and a deviation value for the registration is calculated. A multiplicity of registration methods already employ a deviation value during the registration. This deviation value can be taken over directly as deviation value.

In step S28, a check is subsequently carried out as to whether the registration and determination of the deviation value was already carried out for all comparison data records established in step S24. If this is not the case, the method is repeated from step S25 onward.

After steps S25-S27 were carried out for all comparison data records, the data record whose 3D image data record has the lowest deviation value in the case of registration with the x-ray image is determined as reference data record in step S29.

Subsequently, at least one implantation parameter is determined in step S30. The implantation parameter can simply be determined by virtue of a parameter stored in the reference data record being taken over as implantation parameter. However, additionally it is also possible to segment an implant imaged in the 3D image data record and obtain implantation parameters from the segmentation of the implant. It is also possible to employ a segmentation of the bone in the 3D image data record or an adaptation of a bone model to the 3D image data record in order to determine an ideal value for an implantation parameter. In this case, a three-dimensional bone model is available as intermediate result and an optimization algorithm can be employed to determine the implantation parameter depending on predetermined optimization variables, such as e.g. a maximization of the length of the fastening elements. The implantation parameters can also be determined interactively by superimposed depiction of an implant model on the 3D image data, or by the segmentation data of the 3D image data record and manipulation of the depiction by a user. After determining the implantation parameters, the method ends in step S31.

Figure 4:
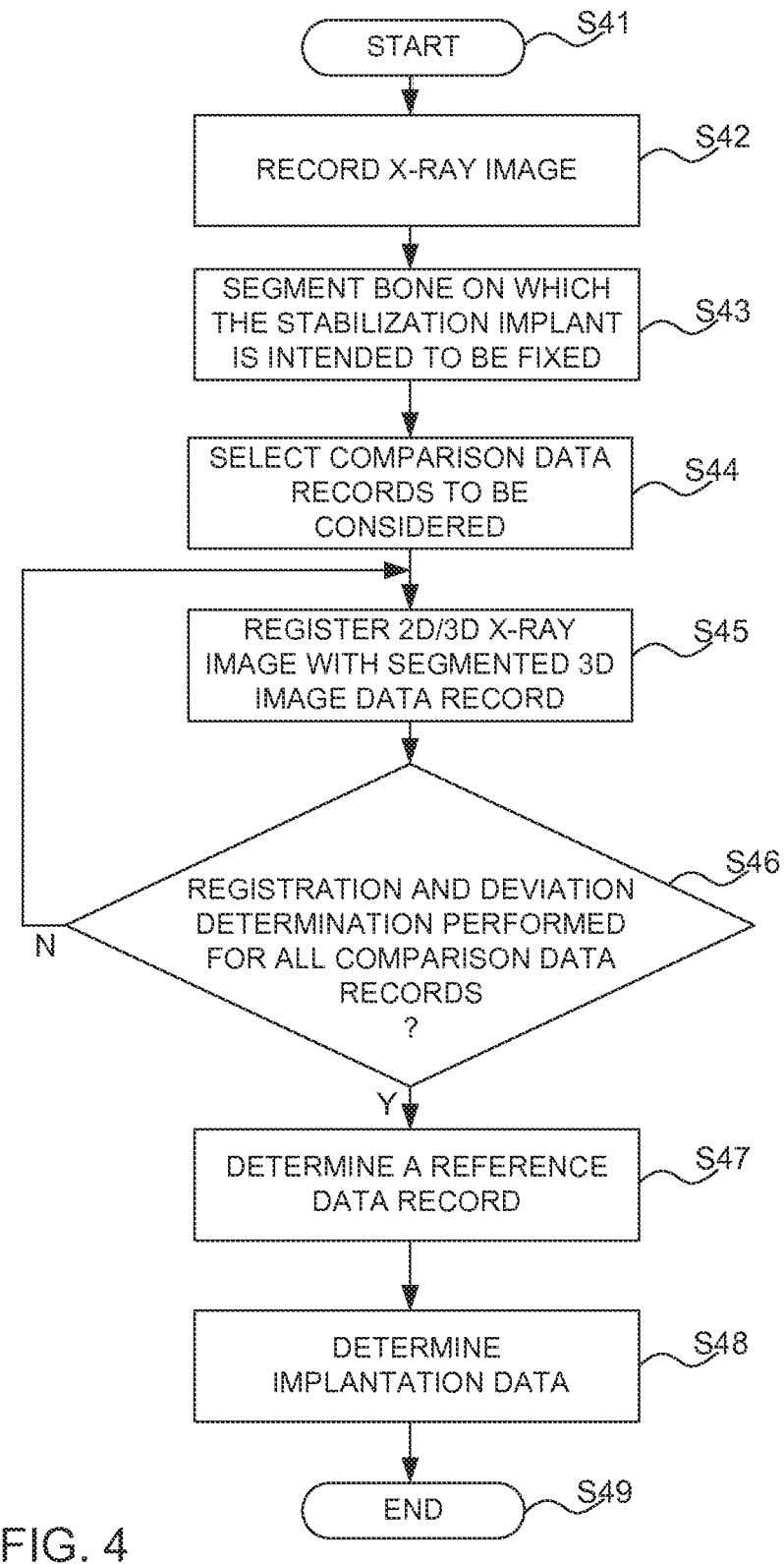
FIG. 4 is a flowchart of a further exemplary embodiment of the method according to the invention.

FIG. 4 shows a further exemplary embodiment of a method for assisting in the treatment of bone fractures. The method depicted in FIG. 4 employs the fact that segmentation information is already stored in the comparison data records in the database. Hence, a faster and more robust method can be achieved under certain circumstances.

After the start of the method in step S41, an x-ray image is recorded in step S42. The start of the method thus corresponds to the method described above. However, for further processing of the x-ray image, a segmentation of at least the bone on which the stabilization implant is intended to be fixed is carried out in the x-ray image in step S43. After the bone was segmented in the x-ray image, there is a selection in step S44 of comparison data records to be considered. This selection takes place similarly to that in step S24. In this case, it is particularly advantageous to employ parameters which were determined in the segmentation of the bone in step S43 also for selecting the comparison data records.

In step S45, there is a 2D/3D registration of the segmented x-ray image with the segmented 3D image data record. Such a registration is particularly simple with segmented data since substantially less data have to be taken into account. Moreover, a deviation parameter is determined in step S45. Said parameter can likewise be determined from the segmentation data; however, it is also possible to determine the deviation parameter directly from the x-ray image and the 3D image data records after successful registration, for example by virtue of a fitting projection of the 3D image data record being produced and a cost function, in particular a standard deviation, subsequently being employed for the comparison of these images. Naturally, it is also possible to employ further-processed data for calculating the cost function. In particular, it is possible to apply edge detectors to the data and/or offsets to be subtracted.

Steps S46-S49, i.e. checking whether the registration and deviation determination was performed for all comparison data records, determining a reference data record, determining the implantation data and the end of the method, correspond to steps S28-S31 of the method described with reference to FIG. 3.

Figure 5:
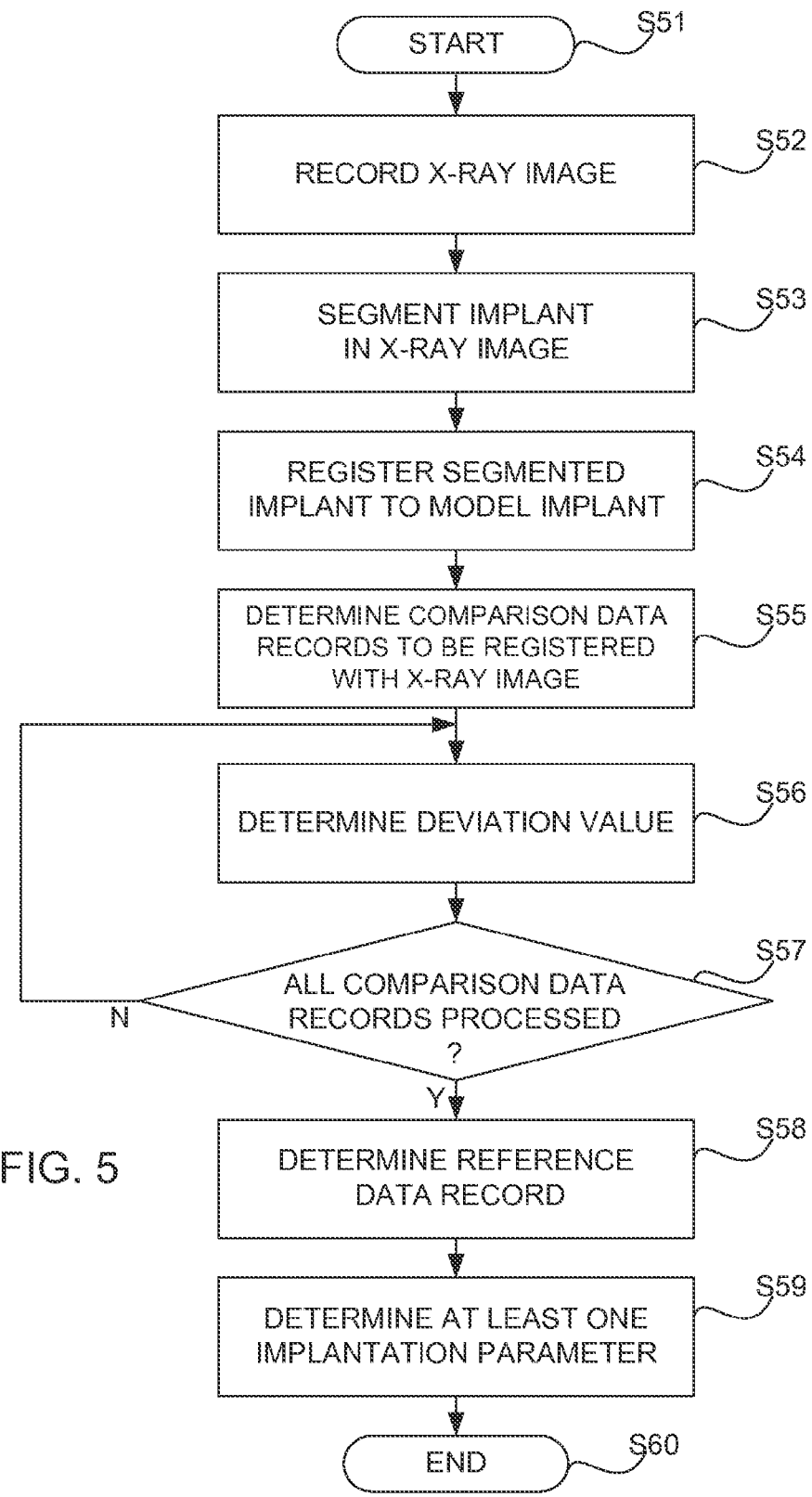
FIG. 5 is a flowchart of a third exemplary embodiment of the method according to the invention.

FIG. 5 shows a flowchart of a third exemplary embodiment of a method for assisting a user in the treatment of bone fractures. A substantial difference to the method already described above is that an image of a stabilization implant is already present in the x-ray image in this exemplary embodiment. Hence, this exemplary embodiment can be employed, in particular, to determine implantation parameters once again after a first positioning of an implant on the bone or to determine further implantation parameters. By way of example, the type of the implant and a first positioning can take place using one of the methods already described above and the method described in the following can be employed subsequently in order to determine, in particular, angle and length of the fastening elements and the precise position of the implant.

However, alternatively or additionally, it is also possible to employ the method described in the following before a stabilization implant is introduced into the body of a treatment object. Thus, it is possible to superpose a virtual implant on the x-ray image within the scope of the method, as will be explained in more detail below. In the subsequent method, the superposition image created here can be employed like an x-ray image which already comprises an implant. By way of example, in this case interactive optimization of a predetermined implant is possible.

After the start of the method in step S51, an x-ray image is recorded in step S52. As described above, the assumption is made in the further description that a stabilization implant is imaged in the image region of this x-ray image, which stabilization implant is already situated in the body of the treatment object. If still no stabilization implant is situated in the body of the treatment object, a virtual implant can be superimposed onto the x-ray image in a step, not shown here, following the recording of the x-ray image in step S52. To this end, a user considering the x-ray image recorded in step S52 selects an implant that he wishes to place into the x-ray image and determines the position and orientation of the implant. Subsequently, the computer apparatus can calculate a superimposed depiction of the implant model and of the x-ray image, which is similar to an x-ray image with an implant at this point. It is therefore possible, in particular, because stabilization implants generally have a substantially stronger absorption than the remaining tissue. Therefore, it is possible to replace the image region which is covered by the virtual stabilization implant by an image of the stabilization implant to simple approximation. Therefore, a virtual x-ray image can be employed during the further course of the method. Whenever reference is made to an x-ray image in all subsequent method steps, this reference can also be read as a reference to a virtual x-ray image.

After recording the x-ray image, the implant in the x-ray image is segmented in step S53. In step S54, the implant segmented in step S53 is registered to a model implant. In particular, there can also be a coordinate transform into the coordinate system of the implant model at this point. Thereupon, a selection of the comparison data records which are to be registered with the x-ray image is determined in step S55. This selection is performed substantially like in step S24 in FIG. 3; however, in step S55, it is particularly advantageous to employ parameters for selecting the comparison data records which describe the implant or the implant position.

The comparison data records are advantageously already transferred into the coordinate system of a model implant.

As a result, it is also no longer necessary to register the 3D image data records since both data records already have the same coordinate system. Thus, a deviation value can be determined directly in step S56. In this case, it is possible, in particular, to employ segmentation information relating to bones stored in the comparison data record and a segmentation of the bones in the 3D image; however, it is also possible to employ a multiplicity of other methods, e.g. as described with reference to step S27 in FIG. 3.

The further steps checking whether all the comparison data records were processed in step S57, determining a reference data record in step S58, determining at least one implantation parameter in step S59 and the end of the method in step S60 correspond to steps S28-S31 of the method described with reference to FIG. 3.

Figure 6:
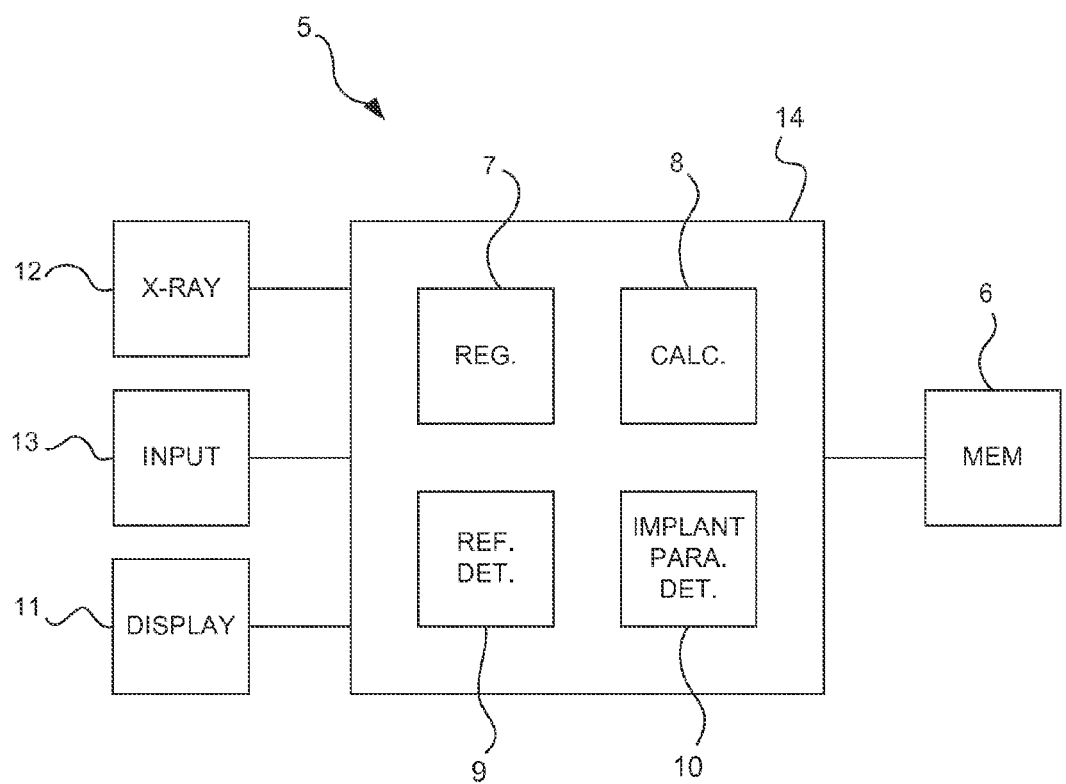
FIG. 6 is a schematic illustration of an exemplary embodiment of a device according to the invention, for assisting a user in the treatment of bone fractures using a stabilization implant.

FIG. 6 schematically shows an exemplary embodiment of a device 5 for assisting a user in the treatment of bone fractures using a stabilization implant. The device has a storage apparatus 6 for providing a database, in which a multiplicity of comparison data records are stored, which comparison data records each comprise at least one 3D image data record of at least one bone, wherein each comparison data record is assigned to an examination object, into which a comparison implant was implanted prior to recording the 3D image data record. A registration apparatus 7 serves for 2D/3D registration of a previously recorded x-ray image with 3D image data records of a selection of the comparison data records determined by a selection criterion or of all comparison data records. Additionally, the device comprises a calculation apparatus 8 for calculating a deviation value, which is a measure for the deviation of the 3D image data record registered with the x-ray image from the x-ray image, for each comparison data record for the 3D image data record of which a 2D/3D registration was performed. A reference determination apparatus 9 is used for determining a reference data record by selecting the comparison data record with the lowest deviation value. An implant parameter determination apparatus 10 serves for determining at least one implantation parameter, which describes a parameter of the implant and/or of a fastening element for fastening the implant, using the reference data record. Additionally, the device 5 has a display device 11 for outputting the representation of the data of the reference data record or of the established implantation parameters.

The device 5 can comprise further components, in particular an x-ray instrument 12 and/or an interface for providing x-ray images, in particular via a network, and also one or more input apparatus 13 for registering user inputs.

In particular, the device 1 is embodied to carry out one of the methods described above.

Naturally, a plurality of the components of the device 5 can also be formed by the same elements. Thus, for example, a single computer apparatus 14 can implement the functions of the registration apparatus 7, the calculation apparatus 8, the reference determination apparatus 9 and the implantation parameter determination apparatus 10. However, the components can also be embodied separately. In particular, the storage apparatus 6 can spatially have a distance from the further components and be connected via a network, in particular the Internet. It is also possible for the registration apparatus 7, the calculation apparatus 8, the reference determination apparatus 9 and the implantation parameter determination apparatus 10 to be connected to the display device 11 and the further components via a network.

It is naturally possible for the features of the exemplary embodiments described above to be combined in various manners.

Although the invention was, in detail, described and illustrated in more detail by the preferred exemplary embodiment, the invention is not thus restricted by the disclosed examples and other variations can be derived there from by a person skilled in the art, without departing from the scope of protection of the invention.

The invention claimed is:

1. A method for assisting a user in a treatment of bone fractures using a stabilization implant, the method comprising:
   accessing a database having stored therein a multiplicity of comparison data records, the comparison data records each containing at least one 3D image data record of at least one bone, wherein each comparison data record is assigned to an examination object, into which a comparison implant was implanted prior to recording the 3D image data record;
   with an x-ray instrument, recording at least one two-dimensional x-ray image of a target bone to which the stabilization implant is to be fastened;
   with a computer apparatus, 2D/3D registering the x-ray image with 3D image data records of a selection of the comparison data records determined by a selection criterion or of all comparison data records and calculating a deviation value, the deviation value being a measure for a deviation of the 3D image data record registered with the x-ray image from the x-ray image, for each comparison data record for the 3D image data record of which a 2D/3D registration was performed by a computer apparatus;
   with the computer apparatus, determining a reference data record by selecting the comparison data record with the lowest deviation value; and
   with the computer apparatus, determining at least one implantation parameter describing a parameter of the implant and/or of a fastening element for fastening the implant, using the reference data record and/or displaying data of the reference data record on a display device of the computer apparatus.

2. The method according to claim 1, which comprises segmenting, with the computer apparatus, a comparison implant imaged in the 3D image data record prior to storing the comparison data record comprising the 3D image data record in the database or when recalling the comparison data record from the database.

3. The method according to claim 2, which comprises not considering the segmented comparison implant during the registration and calculation of the deviation value.

4. The method according to claim 1, which comprises determining the implantation parameter or at least one of the implantation parameters by at least one of the following steps:
   taking over a comparison parameter stored in the reference data record, the comparison parameter describing a parameter of the comparison implant or of a comparison fastening element;
   calculating from the 3D image data record of the reference data record, wherein a segmentation of the 3D image data record is employed and/or a bone model is adapted to the 3D image data record;
   outputting at least one superposition of a two-dimensional representation of the 3D image data of the reference data record and a two-dimensional representation of a three-dimensional implant model and/or of at least one three-dimensional fastening element model on the display device and interactively adapting the implant model and/or the fastening element model by the user.

5. The method according to claim 1, wherein the 2D/3D registration employs an orientation or recording location specification stored in the comparison data record to restrict a search space of the registration parameters.

6. The method according to claim 1, wherein a selection criterion for selecting the comparison data records is a comparison of at least one item of additional information of the imaged bone stored with the comparison data record, a comparison of a bone diameter and/or of information relating to the comparison implant, or a comparison of an image parameter, determined from the respective 3D image data record by the computer apparatus, with a predetermined or predeterminable value.

7. The method according to claim 6, wherein the at least one item of additional information is an age of the patient.

8. The method according to claim 6, wherein the image parameter is a parameter determined by segmenting the 3D image data record.

9. The method according to claim 1, which comprises displaying the implantation parameter on the display device.

10. The method according to claim 9, wherein a representation is graphical and displays an implant model and/or at least one fastening element model.

11. The method according to claim 1, which comprises, prior to recording the x-ray image, arranging a calibration body in the image region of the x-ray image for size calibration.

12. The method according to claim 1, which comprises, for target bones that are mirror-symmetrically present twice in the body of an examination object, utilizing also comparison data records from the 3D image data record with images of a mirror-symmetrical bone of the target bone when registering and calculating the deviation value, and thereby mirroring one or the x-ray image or the 3D image data record.

13. The method according to claim 1, which comprises, after introducing the implant into the body of the examination object, recording at least one further x-ray image and determining at least one implantation parameter anew and/or determining a further implantation parameter.

14. The method according to claim 1, wherein the implantation parameter or one of the implantation parameters is selected from the group consisting of an implant type, an implant position, a fastening element type, a fastening element length and an introduction angle of at least one fastening element.

15. The method according to claim 1, which comprises segmenting a 3D image data record prior to storing the comparison data record comprising the 3D image data record in the database and storing the segmentation data in the comparison data record, wherein the segmentation data are employed in the 2D/3D registration and/or the calculation of the deviation value and/or of the implantation parameter.

16. The method according to claim 1, which comprises, prior to storing the comparison data record in the database or when recalling the comparison data record from the database, segmenting the comparison implant in the 3D image data record and registering with a model implant by the computer apparatus and transforming a coordinate system of the 3D image data record into a coordinate system of the model implant.

17. A device for assisting in a treatment of a bone fracture using a stabilization implant, the device comprising:
 a storage apparatus (6) with a database containing a multiplicity of comparison data records, the comparison data records each containing at least one 3D image data record of at least one bone, wherein each comparison data record is assigned to an examination object into which a comparison implant was implanted prior to recording the 3D image data record;
 a registration apparatus (7) for 2D/3D registration of a previously recorded x-ray image with 3D image data records of a selection of the comparison data records determined by a selection criterion or of all comparison data records;
 a calculation apparatus (8) for calculating a deviation value, the deviation value being a measure of a deviation of the 3D image data record registered with the x-ray image from the x-ray image, for each comparison data record for the 3D image data record of which a 2D/3D registration was performed;
 a reference determination apparatus (9) for determining a reference data record by selecting the comparison data record with the lowest deviation value;
 an implant parameter determination apparatus (10) for determining at least one implantation parameter, which describes a parameter of the implant (1) and/or of a fastening element for fastening the implant (1), using the reference data record; and
 a display device (11) for outputting the representation of the data of the reference data record or of the established implantation parameters.

18. The device according to claim 17, configured for carrying out the method according to claim 1.

* * * * *